United States Patent
Cocola et al.

(10) Patent No.: US 6,832,722 B1
(45) Date of Patent: Dec. 21, 2004

(54) METHOD AND MEANS FOR DATA MANAGEMENT IN A LABORATORY

(75) Inventors: Adriano Cocola, Siena (IT); Michele Meloni, Siena (IT)

(73) Assignee: Diesse Diagnostica Senese S.p.A., Milan (IT)

( * ) Notice: Subject to any disclaimer, the term of this patent is extended or adjusted under 35 U.S.C. 154(b) by 0 days.

(21) Appl. No.: 10/088,320

(22) PCT Filed: Sep. 12, 2000

(86) PCT No.: PCT/IT00/00359

§ 371 (c)(1), (2), (4) Date: May 29, 2002

(87) PCT Pub. No.: WO01/20532

PCT Pub. Date: Mar. 22, 2001

(30) Foreign Application Priority Data

Sep. 15, 1999 (IT) .......................... FI99A0191

(51) Int. Cl.[7] .............................. G06F 17/60
(52) U.S. Cl. .................. 235/385; 235/375; 235/462.01; 235/472.01; 235/470; 235/474
(58) Field of Search ................................. 235/385, 375, 235/462.01, 472.01, 470, 474; 436/43, 46, 48

(56) References Cited

U.S. PATENT DOCUMENTS

| | | | |
|---|---|---|---|
| 3,831,006 A | | 8/1974 | Chaffin, III et al. ........ 235/375 |
| 4,678,894 A | * | 7/1987 | Shafer ......................... 235/375 |
| 4,857,713 A | | 8/1989 | Brown ......................... 235/375 |
| 5,164,575 A | * | 11/1992 | Neeley et al. ......... 235/472.01 |
| 5,663,545 A | * | 9/1997 | Marquiss ..................... 235/375 |
| 5,735,387 A | * | 4/1998 | Polaniec et al. ......... 198/690.1 |
| 5,842,179 A | * | 11/1998 | Beavers et al. ............... 705/28 |
| 5,888,825 A | * | 3/1999 | Carr et al. ..................... 436/48 |
| 6,141,602 A | * | 10/2000 | Igarashi et al. ............. 700/226 |
| 6,428,640 B1 | * | 8/2002 | Stevens et al. ............... 156/64 |

FOREIGN PATENT DOCUMENTS

| | | |
|---|---|---|
| EP | 0 510 615 A1 | 10/1992 |
| EP | 0 819 470 A1 | 1/1998 |

* cited by examiner

*Primary Examiner*—Steven S. Paik
(74) *Attorney, Agent, or Firm*—McGlew and Tuttle, P.C.

(57) ABSTRACT

A method for data management in an analytical laboratory and a data management system include containers provided for the laboratory analysis of biological specimens. Each container is associated with its own identification code. A patient code is associated with a patient to be subjected to analysis. For each container used for a patient, a combination of a patient code and the identification code of the corresponding container is generated in a data processing system. At least one analyzer is used to carry out at least one analysis on the container or containers used for the patient. The analyzer enters the results of the analysis, combined with the identification code of the container or containers, into the data processing system.

19 Claims, 5 Drawing Sheets

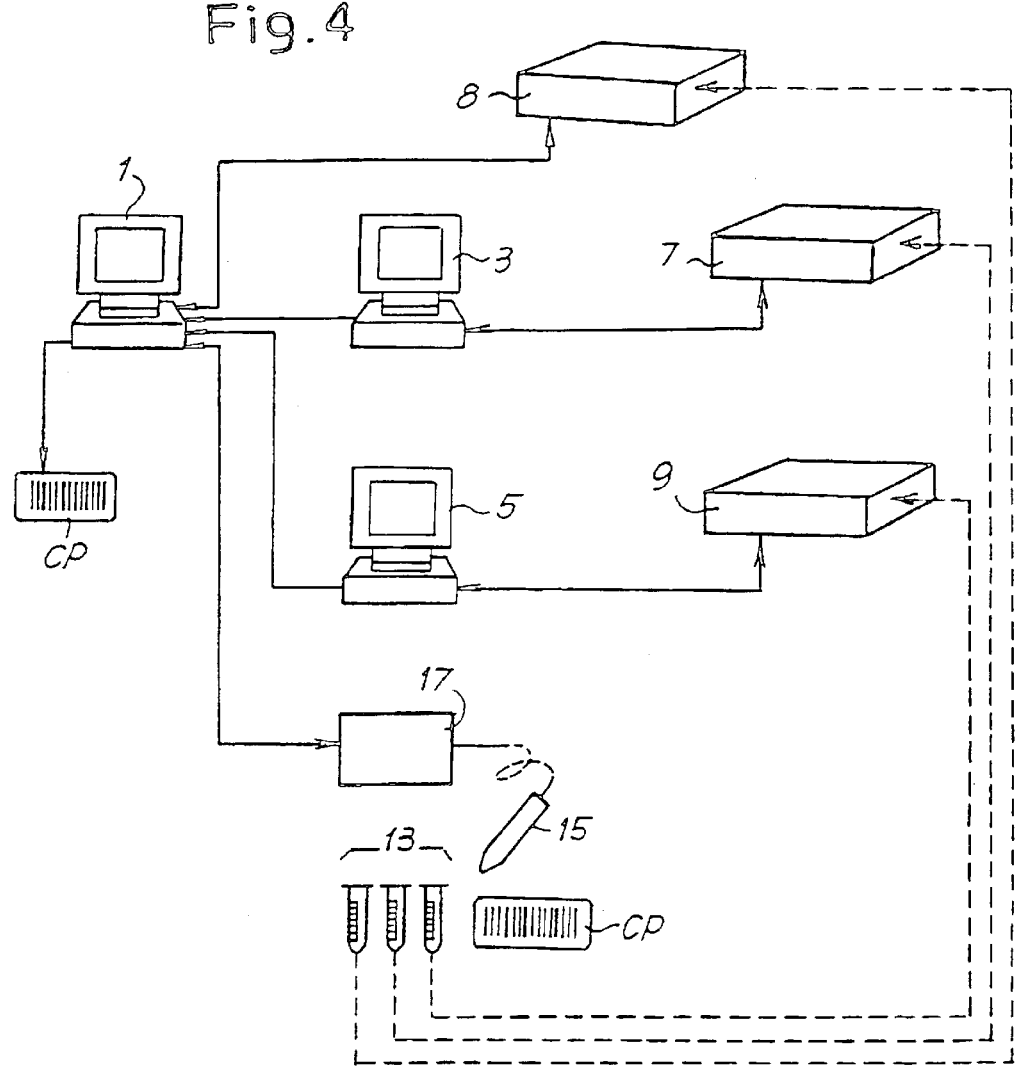

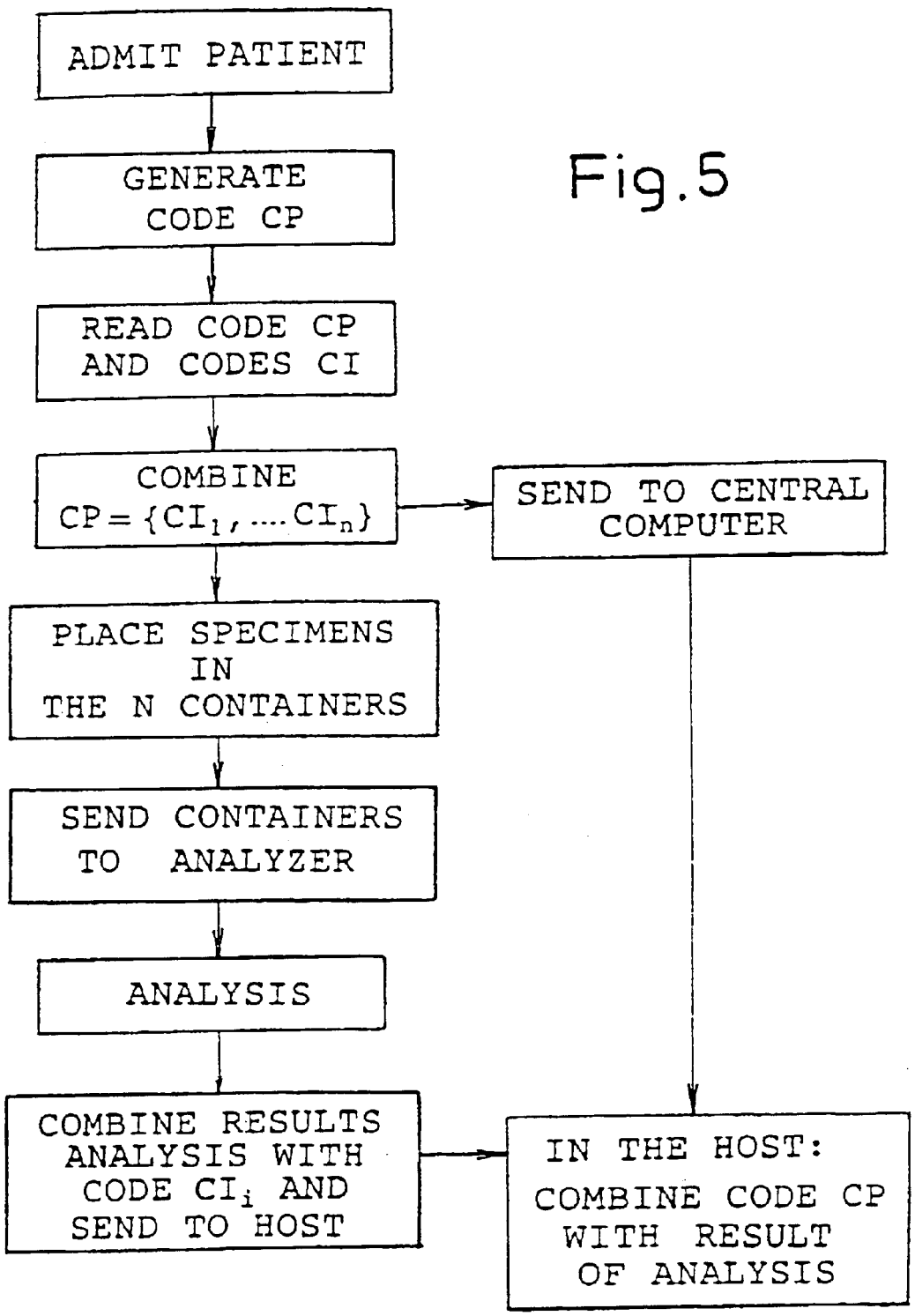

METHOD AND MEANS FOR DATA MANAGEMENT IN A LABORATORY

This application is a 371 of PCT/IT00/00359 filed on Sep. 12, 2000.

TECHNICAL FIELD

The present invention relates to a method for data management in an analytical laboratory, particularly in a laboratory for analyzing biological specimens from patients.

The invention also relates to a system for data management in an analytical laboratory.

Finally, the invention relates to a container for use in the method and with the system mentioned above.

PRIOR ART

In the era of total quality, high standards of safety and reliability are required in the diagnostic field as in other areas. In spite of the efforts made by manufacturers of equipment and materials for diagnostic analysis, however, situations occur in the course of application in the analytical laboratory and/or in a hospital complex which give rise to errors and thus reduce the quality of the results obtained.

At the present time, containers of various types, particularly test tubes, cups, racks, microplates and others, are used for carrying out a multiplicity of analyses of the diagnostic type. In the present description and the following claims, the term "container" denotes any device suitable for containing a biological specimen to be analyzed. The specimen can be a biological specimen (for example blood, serum or urine) or a specimen of a different kind, for example a fragment of tissue, or even a DNA specimen. The container can be a container in which has been placed the specimen taken directly from the patient, or a container in which has been placed a fraction of a specimen taken previously and placed in an intermediate container. In this case, reference is made, for example, to a "mother test tube" and a "daughter test tube". The containers can be simple vessels for the biological specimen, or can also contain a preparation which is designed to react with the specimen for the execution of the subsequent analyses.

In the present description and the attached claims, the term "analytical laboratory" denotes any structure in which analyses of the diagnostic type or the like are carried out on biological specimens taken from patients.

There are currently various methods for data management in analytical laboratories, which also vary in respect of the degree of automation of each structure. For example, in a particularly simple management method, the patient's name is handwritten on a white label provided on the container. In a more advanced method, a patient code is associated with each patient whose data are acquired by a central computer (Host Computer). In the subsequent processing, the patient is identified by means of the patient code instead of by his own forename and surname. In this case, it is the patient code that will be written on the white label applied to the container.

In other procedures, a sheet with attached self-adhesive labels bearing the patient code in the form of a bar code is printed at the moment of generation of the patient code. The patient will then go with these labels to the specimen-taking center, where the operator will take the biological specimen, for example blood. In this case, the operator does not have to write the name or the patient code on the white label previously applied to the container, but can simply detach the self-adhesive label from the sheet supplied by the patient and apply the label to the container in which the biological specimen for analysis is placed.

The container or containers identified in this way are then sent to one or more pieces of equipment which carry out the required analyses. In the present description, these pieces of equipment will be indicated summarily by the term "analyzers". The term "analyzer" denotes any equipment capable of carrying out an analysis on a biological specimen. While carrying out analyses, the analyzers acquire the patient code appearing on the container and then combine the patient code with the result of the analysis. The analyzers can be controlled by their own incorporated microprocessors, by electronic computers interfaced with the analyzers, or by a remote computer, for example the central computer which has acquired the patient data and generated the patient code.

In some cases, one or more containers are sent to pieces of equipment which take the biological specimen from a single container ("mother test tube") and distribute it into other containers ("daughter test tubes"), for carrying out different analyses on the same specimen. In this case, the pieces of equipment are programmed according to a job sheet so that they are capable of determining which containers the fractions of the biological specimen of which patient have been distributed into.

The analyzers and any machines which distribute the specimen from "mother" test tubes to "daughter" test tubes are connected to the central computer in a suitable way. The central computer thus receives the results of the analyses carried out by the various analyzers associated with the patient codes of the individual patients initially acquired. In this way it proceeds to print the report.

Even if there is maximum automation of the data management system in the analytical laboratory, errors due to various causes may occur and give rise to serious consequences in that the patients receive results relating to biological specimens of different patients.

A first set of errors originates from the system of labeling with patient codes. A first and more evident error is the human error which consists in attaching a label bearing the bar code of a patient to the wrong container. This error is commonly caused by the uncomfortable conditions in which the personnel have to work in the specimen-taking room.

This is because the operator in the specimen-taking center is in direct contact with the biological material from which he must protect himself by using, at least, rubber gloves, and in these conditions he must detach the adhesive label with the printed patient code and attach it to the patient specimen-taking container in front of him after having identified it on the job sheet.

Specimen-taking containers vary according to their manufacturers, and this gives rise to numerous problems, since the area for the application of the label to the container is not always compatible with the size of the label. Additionally, the label has to be applied to the container so that it is as straight as possible, to prevent the analyzer reading system, which is specific for each piece of equipment, from having difficulties in identification, from identifying the label incorrectly, or from being simply unable to read it. In this respect, the quality of printing of the patient code printed by the central computer is also very important, since there are considerable differences in sensitivity between different code readers, according to the type and programming of each reader.

The consequences of all these possible events can easily be imagined; they range from the allocation of a different result to the blocking or slowing of the data stream of the routine, due to bottlenecks in the patient code recognition model downstream of the central computer.

The use of a sheet carrying a plurality of self-adhesive labels, the number of which usually exceeds that of the containers which are actually to be used, is a source of waste, since for each patient several unused labels are frequently thrown away. The presence of left over labels increases the risk that left over labels will be erroneously applied to containers for a different patient. Moreover, the use of self-adhesive labels makes it necessary to print the whole patient sheet on self-adhesive material which is expensive.

The operation of detaching and applying the adhesive labels is time-consuming and laborious and reduces the time available for personnel responsible for specimen taking, thus increasing the waiting time for specimen taking. In certain cases, this drawback is overcome by the employment of an auxiliary operator responsible solely for applying the labels, so that the person taking the specimen is released from this task. However, this significantly increases personnel costs, or diverts personnel from more important activities.

The overall quality of the result is ultimately affected by this.

There are also difficulties due to the lack of a uniform standard applied in the field. Indeed, when two or more systems interact and have to exchange data, it is necessary to identify a simple, reliable model that is as general as possible (the "standard"), to which all the elements of the system must conform.

The systems currently in use in various laboratories for the flow of data between analyzers and the central computer give rise to the following paradox. On one hand, the manufacturers of diagnostic systems market a vast range of instruments and containers which have a high level of internal compatibility. On the other hand, there are companies (software houses), managing the data processing systems of the analytical laboratories, which produce models that are similar to, but different from, each other. The instruments are interfaced with the network. The laboratory personnel has to make the various components (analyzers, containers, management programs of the central computer and the network) compatible with each other to some degree, while minimizing costs and errors.

The paradox lies in the fact that neither the manufacturers nor the software houses have a model which can act as a standard, and consequently, whenever a manufacturer's new data processing system is installed in a laboratory, considerable efforts are required to make the system compatible, and this also happens in each laboratory for all the new instruments that arrive.

OBJECTS OF THE INVENTION

A first object of the present invention is to provide a method and a system for laboratory data management which makes it possible to minimize management errors and thus improve the quality of the system.

A further object of the present invention is to provide a system and a method which enable data to be managed in an analytical laboratory in a more reliable way and with savings of materials and personnel.

Yet another object of the present invention is to provide a system and a method which enable equipment and containers from different sources to be made easily compatible, without the requirement for major adaptation work in the programming and design of the data processing system.

An object of the invention is also to provide a data management method which can be applied in existing systems, without the necessity of modifying the communication protocols of the computer network, and without the necessity of reprogramming the computers themselves.

Another object of the invention is to provide a system and a method which enable manufacturers to produce analyzers and containers in which the quality of the reading of the codes applied to the containers is optimized, while bottlenecks, slowing of the data stream, and reading errors are reduced.

BRIEF DESCRIPTION OF THE INVENTION

These and other objects and advantages, which the following text will make clear to persons skilled in the art, are achieved with a method comprising the steps of:

providing a plurality of containers for the laboratory analysis of biological specimens, each container being associated with its own identification code;

associating a patient code with a patient to be subjected to analysis;

for each container used for said patient, generating in a data processing system a combination of said patient code with said identification code of the corresponding container;

carrying out, by means of at least one analyzer, at least one analysis on the container or containers used for said patient, the analyzer entering the results of said analysis, combined with the identification code of the container or containers, into the data processing system.

This method is characterized in practice in that each container used for the biological specimens is identified by its own identification code. This code can be applied during the production of the container, directly by the manufacturer, who can thus carry out the labeling (or other means of applying the identification code) in an optimal way, according to (a) the characteristics of the container; (b) the characteristics of the code reader with which any analyzer produced by the same manufacturer is equipped. The method according to the invention therefore has the advantage that each analyzer has to read, with its own reader, only one identification code which has advantageously been applied to the container by the manufacturer of the container, who may also be the manufacturer who has produced the analyzer. Thus there is an optimal level of compatibility between the container (and its code) and the analyzer (and its reader), with consequent elimination of reading errors.

The patient will be provided with a single medium bearing his own patient code, instead of a set of self-adhesive labels. The printing of the medium bearing the code is fast and economical. There is no waste of material, and it is not necessary to use expensive self-adhesive material.

The operator responsible for specimen taking does not have to carry out any complex operation of detaching and applying adhesive labels, but can simply read the patient code and the identification codes of the container or containers, thus causing the data processing system to acquire these codes which are combined with each other. Therefore, the human errors due to incorrect combination of adhesive labels with containers are eliminated. The acquisition of the codes is extremely rapid and requires a minimum of manual activity, and can easily be carried out even when protective rubber gloves are worn.

In greater detail, the method according to the present invention can be implemented with the following steps:

generating a patient code for at least one patient on whom at least one analysis is to be carried out and storing said patient code in a data processing system. This operation is carried out at the moment of admission of the patient, by means of the central computer;

placing a biological specimen from said patient in said at least one container. This operation is carried out, for example, in the specimen-taking room in the case of a blood specimen. In this step, the operator causes the data processing system to read the patient code and the identification codes of the containers used;

carrying out at least one analysis of said specimen in at least one analyzer. In this step, the analyzer automatically reads (by means of its own reader) the identification code of the container and enters it into the data processing system to which it is connected, while associating it with the results of the analysis;

using the data processing system to associate the results of the analysis or analyses with the patient code, and then with the patient identified by said patient code, by means of the combination of the patient code with the identification code.

The method has the further advantage that the data processing system holds data in which the result of each analysis is combined with an identification code which identifies in a unique way the container of the analyzed specimen. This facilitates any quality control, for example where the result of the analyses is disputed. The problems related to anti-doping analysis may be considered in this connection.

Theoretically, the patient code and the identification code can be codes of various types, for example alphanumeric codes which the operator responsible for specimen taking and any operator responsible for running the analyzer enter into the data processing system by means of a keyboard. However, in accordance with what has already been implemented, these codes are advantageously automatically readable codes, so that the intervention of the operators is minimized. For example, they may be bar codes or other optical reading codes. In this case, the operator responsible for specimen taking, or an assistant, can cause the patient codes and the identification codes to be read to a unit of the data processing system by means of an optical reader wand or other reader. Alternatively, the codes can be magnetic codes. This can be the case with the patient code in particular, since the patient could be provided with a magnetic card bearing his personal data and his patient code, supplied by the analytical laboratory to the patient on his first admission. The card can then be used for subsequent services provided by the same laboratory. Optical reading codes (particularly bar codes) may be preferable for the identification of the containers, since analyzers are now already equipped with optical readers. The use of patient codes and identification codes of the same kind, readable with the same instruments, simplifies the operations of acquiring and combining these codes in the data processing system.

The method according to the present invention can easily be implemented in an existing management system of the type described above. Indeed, in a possible embodiment, it is provided that: (a) the patient code is generated by a central computer of the data processing system by a similar method to that used up to the present, with the difference that the code can be printed on a single plain paper medium and not on a set of self-adhesive labels; (b) the combination of the patient code with the identification code is carried out by means of a unit of the data processing system other than the central computer, and therefore this unit can be suitably programmed and interfaced without interfering with the programming of the central computer; and (c) the result of the analysis, sent to the central computer, is associated directly with the patient code, rather than with the identification code of the container. Thus the central computer continues to receive at its input the same data for whose management it is currently programmed (patient code; result of the analyses from the analyzer). The difference from the conventional method consists in the fact that the analyzer reads the identification code of the container, instead of the patient code, which has been produced and applied to the container in an optimal way with respect to the characteristics of the reader of the analyzer. The result of the analysis, combined with the identification code of the container of the analyzed specimen, is then processed further to recombine it with the patient code which is combined with the identification code. The latter data item (patient code+result of the analysis) is the one that will be sent to the central computer, in a way completely identical to that used in conventional systems. The recombination of the result of the analysis and the patient code can be carried out by means of the same unit which has carried out the combination of the patient code with the identification code, or by means of a different unit.

In this embodiment, the method can be implemented in existing systems and can be executed even when analyses of the conventional type, in other words those using the conventional combination of container and patient code, are carried out in the same system. This is because the basic elements of the data processing system continue to operate in conventional ways, the operations relating to the method according to the present invention being "transparent" to the central computer.

In an improved embodiment of the method according to the invention, however, the central computer can be programmed to receive from the individual analyzers the results of the analyses combined with the identification codes of the containers. In this case, the same central computer will receive, from the unit supplied to the operator in the specimen taking room, the combination of the patient code and the identification codes of the containers assigned to the individual patient, and will be programmed in such a way that the patient code is re-associated with the results of the analyses by means of the aforesaid combination. In this embodiment, the method permits simpler processing of the data, but requires the reprogramming of the data processing system and makes it necessary to carry out all analyses by the new method, in other words to have all the containers identified by corresponding identification codes.

On the other hand, in this improved embodiment the method can be used to carry out in a simple way, using the same procedure, even those analyses in which the biological specimen contained in a mother test tube is distributed into a plurality of daughter test tubes, for clinical chemical analysis for example. This is because each daughter test tube will be provided in its turn with an identification code. The equipment which carries out the distribution will read the identification code of the mother test tube and the identification codes of the daughter test tubes and will enable the data processing system (in the central computer directly, for example) to create a combination of the former and the latter, in a way similar to the combination created between the patient code and the identification code of the mother test tube. The combination can also be carried out in a semi-automatic way by an operator using an optical reader wand or other suitable device to read the identification codes of the mother test tube and the daughter test tubes before entering them into the distribution device. The results of the analyses will then be combined with the identification codes of the daughter test tubes. Using a reverse process with a number of steps, it is always possible to combine the results of the analyses with the original patient code. The reverse process will have a number n of steps, with n=m+1 where m is the number of mother-daughter relations.

When the biological specimen is distributed in a rack or in a microplate, where the individual wells cannot be characterized by identification codes, and where specimens from a plurality of patients are placed in wells in the same microplate or in the same rack, the rack or the microplate will have its own identification code and the individual wells will be identified by coordinates. The analyzer which automatically distributes the biological specimens among the different wells uses a job sheet to associate the identification code of the container from which it takes the specimen with the coordinates of the well or wells of the microplate or rack into which it distributes the fractions of the specimen.

The data processing system according to the invention comprises, in combination,

- a central electronic computer, for acquiring the data on patients on whose biological specimens the analyses are to be carried out, and for generating a patient code for each patient acquired;
- means for acquiring an identification code associated with each container of a plurality of containers for laboratory analysis of biological specimens;
- means for combining each of said acquired identification codes with a corresponding patient code;
- at least one analyzer with means for reading identification codes associated with the containers which are placed in it, said analyzer carrying out at least one analysis on a biological specimen contained in the containers placed in it and supplying to said electronic computer the result of the analyses carried out, combined with data capable of associating said result with the patient to whom the biological specimen belongs.

Further advantageous embodiments of the method and system according to the invention are indicated in the attached claims.

For the application of the method according to the invention, a container for laboratory analysis of biological specimens is provided; this is characterized in that it is provided with an identification code which is unique or absolute, in other words different from those of the other containers used in the laboratory, and preferably of the automatically readable type, to enable the use of the method to be automated and simplified. The container, or the set of containers, each characterized by its own absolute identification code, also constitute an object of the present invention.

The container may also be provided with an expiry date, after which the container shall not be used. This date can be included in the identification code and/or written in a man-readable form. In the first case, the system in which it is used can be programmed such as to interrupt the analysis if an expired container has been used, this situation being automatically detected by reading the identification code. Additionally or alternatively, the container may be provided with means which render it unusable after the expiry date. For example, for those containers which must be transparent for optical reading, the material they are made of can be such that it becomes opaque after the expiry date. In addition or alternatively the identification code can be printed with an ink which becomes unreadable after the expiry date.

BRIEF DESCRIPTION OF THE DRAWINGS

The invention will be more clearly understood from the description and the attached drawing, which shows a practical and non-restrictive embodiment of the invention. More particularly, the drawings show, in FIG. 1, a diagram of a network consisting of a central computer and a set of peripheral units;

in FIG. 4, a diagram of a network similar to that of FIG. 1, in a second embodiment; and in FIG. 5, a flow chart representing the method according to the invention in a second embodiment.

DETAILED DESCRIPTION OF EMBODIMENTS OF THE INVENTION

Figure 1:
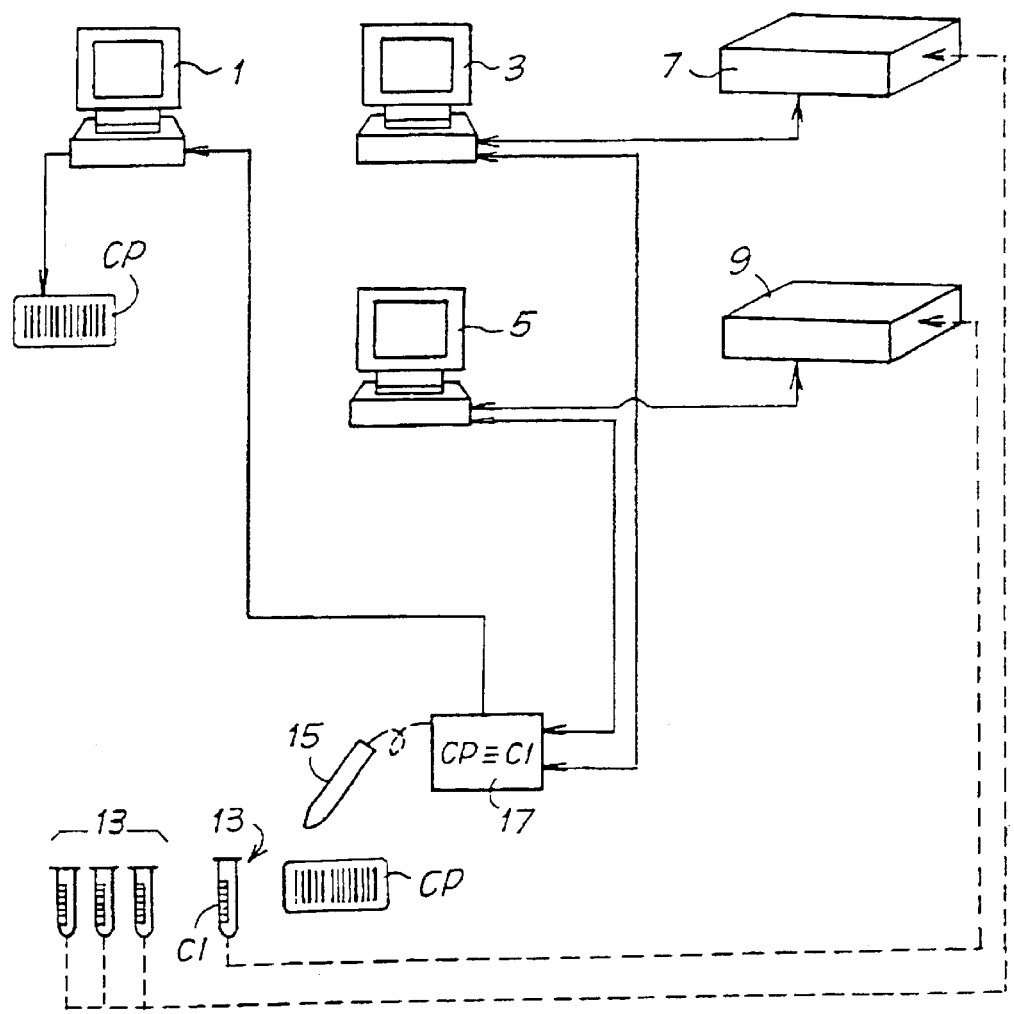

FIG. 1 shows schematically a network of units forming a data processing system in which the method according to the present invention can be implemented. The number 1 indicates a central electronic computer (host computer). The central computer 1 is programmed to acquire the patient data and to generate for each patient a patient code CP, which for example is printed in the form of a bar code on a paper medium.

The numbers 3 and 5 indicate two peripheral electronic computers for monitoring and operating corresponding analyzers 7 and 9. The patient whose data have been acquired by the central computer 1 and for whom a patient code CP has been output passes into an area for taking biological specimens, showing his patient code CP, and here an operator takes the specimen and places, for example, the blood (or other biological specimen) in one or more containers 13. Each container 13 is provided with an identification code CI, which is unique and absolute, in other words different for each container 13, for example a bar code printed on a self-adhesive label applied to the container 13 during the production of the container.

Figure 2:
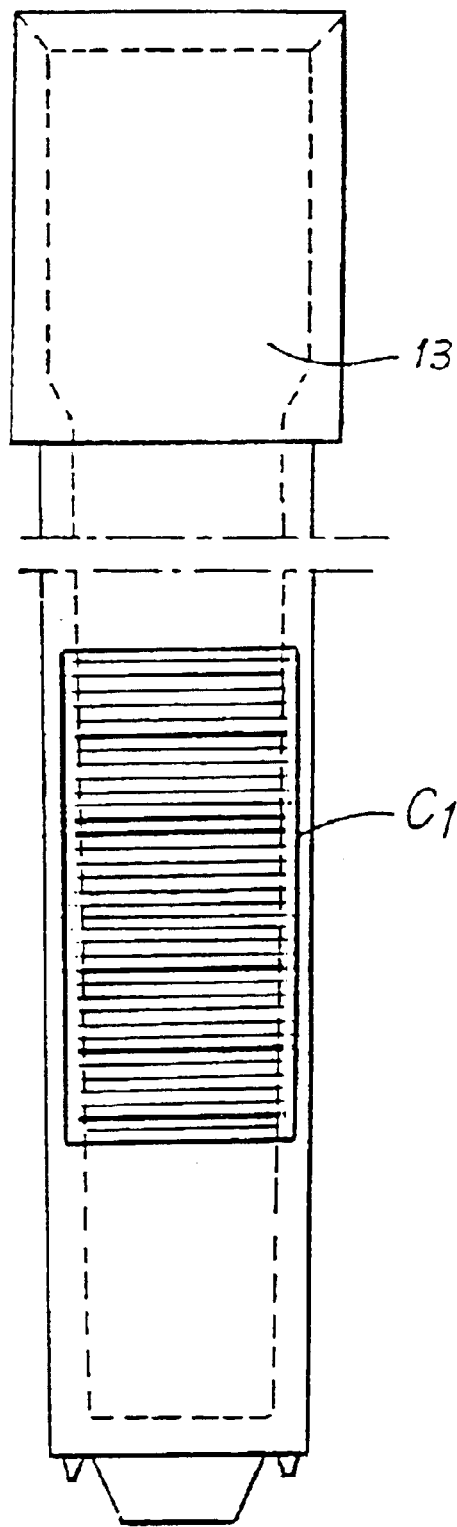
in FIG. 2, an example of a container with an identification code.

An example of a container in the form of a test tube for ESR (erythrocyte sedimentation rate) analysis with its corresponding identification code CI is shown in detail in FIG. 2.

Using an optical reader wand or other equivalent reading device, indicated schematically by 15, the operator who takes the specimen, or his assistant, reads the patient code CP and the identification codes CI of the containers 13 which have to be used for this patient. The number 17 indicates a generic control unit of the reader 15 which acquires the codes CP and CI. The unit 15 can be programmed to permit the acquisition of a patient code and an unlimited number (or a number limited to a maximum) of identification codes relating to the same number of other containers. Software can be used to ensure that it is not possible to read, for example, two patient codes consecutively, in order to prevent errors, and/or that it is not possible to acquire a patient code after the acquisition of a preceding patient code and one or more identification codes CI without the execution of a reset operation.

Thus the unit 17 enables the codes CI and CP, combined with each other, to be entered into the data processing system: each patient code CP will be associated in the data processing system with one or more identification codes CI, relating to the containers in which the operator has placed the patient's biological specimens.

The data read by the unit 17 are sent to the computers 3 and 5 by means of a data line or other suitable means, if necessary by physically transferring a storage medium such as a diskette or other. The specimens in the containers 13 are transferred physically to the analyzers 7, 9 (as shown by the arrowed broken lines).

The analyzers 7 and 9 comprise corresponding readers (not shown) which read the identification codes CI of the containers 13 placed in them and carry out the specified analyses. Since each type of analysis frequently requires a specific type of container, it is possible to make the identification code CI of the individual container contain additional data relating to the type of analysis for which it is intended. For example, specific containers in which a special reagent is kept can be provided for specific clinical chemical analyses, the type of reagent (and therefore the type of analysis) being indicated by one or more digits of the identification code. At the same time, to enable the operator to easily identify the type of container, containers for different analyses can be distinguished by different shapes, or caps of a particular color for each type of container.

The analyzer receiving a container holding the biological liquid to be analyzed can check, by reading the identification code CI, that the type of analysis for which the container is intended corresponds to the analysis which the analyzer is to carry out, and can emit an error signal when this is not the case.

To enable the different analyzers to determine which analyses are to be carried out for the individual patients, it is possible to use a job sheet by a method similar to that used in conventional systems. The central computer 1 generates a job sheet where the patient code and the type of analysis to be carried out is shown for each registered patient. These data are then entered by an operator by means of a keyboard into the individual analyzers or into the computers controlling them. Any errors at this point do not cause particular problems, being limited to the possible performance of analyses which were not requested or the omission of analyses which were requested. However, there is no possibility of the occurrence of errors of incorrect combination of the patient data with the results of the analysis.

The analyzers 7 and 9 carry out the requested analyses under the control of the computers 3, 5, and send to the computers 3, 5 the results of the analyses combined with the identification codes CI read from the individual containers 13. These data are then sent to the unit 17 (or another unit which stores the combination of the code CP and the codes CI generated by the unit 17 by the reading of the codes). The unit 17 is connected to the central computer 1 and supplies it with the results of the analysis after it has recombined these with the patient codes on the basis of its knowledge of the correct combination of the identification codes CI (combined with the results of the analyses obtained from the computers 3, 5) and the patient codes CP. The central computer 1 can thus receive the results in the conventional standard format at its input, and does not require reprogramming to execute the described method.

Figure 3:
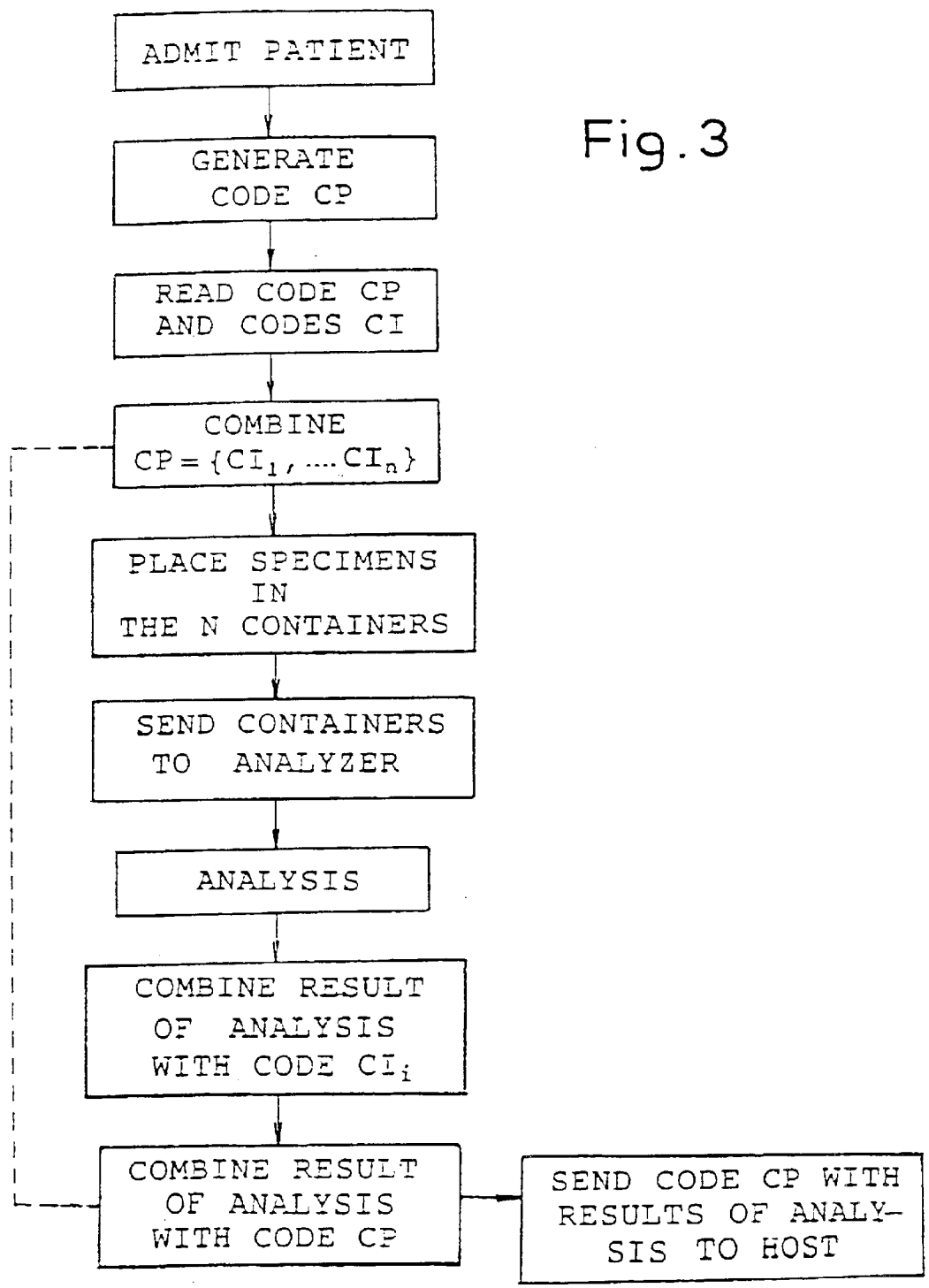
in FIG. 3, a flow chart representing the method according to the invention in a first embodiment.

FIG. 3 summarizes the procedure described above, in the form of a flow chart.

When the central electronic computer 1 can be programmed in a dedicated way, the system for implementing the method according to the present invention can be simplified as shown in the diagram in FIG. 4, where identical or equivalent parts are indicated by the same reference numbers. This diagram additionally shows an analyzer 8 controlled directly by the central computer 1. The unit 17 is connected directly to the central computer rather than to the peripheral computers 3 and 5. The codes CI combined with each individual code CP read by the reader 15 are thus communicated by the unit 17 to the central computer 1. This computer receives the results of the analyses, combined with the corresponding identification codes CI of the containers 13 either by the analyzers directly (in the case of the analyzer 8) or by the peripheral computers 3, 5 which control the analyzers (in the case of the analyzers 7 and 9). The central computer 1 is programmed so that it can recombine the results of the analyses with the corresponding patient codes CP and then print the results in clear text, by means of the combination communicated by the unit 17.

When—for example as shown schematically in FIG. 4—there is a connection between the central computer and the peripheral computers associated with the individual analyzers, it is no longer necessary to supply the job sheet and enter into the individual analyzers the data relating to the types of analysis to be carried out on the individual patients. These data are supplied directly to the peripheral computers by the central computer 1 which has acquired the patient.

The embodiment of the method described above is summarized in the block diagram in FIG. 5, where (in a similar way to that used in FIG. 3) the symbols $CI_1 \ldots CI_n$ indicate the n identification codes of the n containers 13 combined with a given patient code P.

It is to be understood that the drawing shows only a possible embodiment of the invention, which can be varied in its forms and arrangements without departure from the scope of protection specified by the following claims.

What is claimed is:

1. A method for data management for an analytical laboratory, the method comprising the steps of:

providing a plurality of containers for the laboratory analysis of biological specimens, each container being associated with a unique identification code of said container and having a marking including said unique identification code applied to said container during production or packaging of said container;

associating a patient code with a patient to be subjected to analysis;

for each container used for said patient, generating in a data processing system a combination of said patient code and said unique identification code of the corresponding container;

carrying out, by means of at least one analyzer, at least one analysis on the container or containers used for said patient, the analyzer entering the results of said analysis, combined with the unique identification code of the container or containers, into the data processing system.

2. The method according to claim 1, comprising the steps of:

generating a patient code for at least one patient on whom at least one analysis is to be carried out and storing said patient code in a data processing system;

placing a biological specimen from said patient in said at least one container;

carrying out at least one analysis of said specimen in at least one analyzer, the analyzer reading the unique identification code of said container and entering into said data processing system the results of the analysis combined with the unique identification code of said container;

using said data processing system to associate the results of the analysis or analyses with the patient code, and then with the patient identified by said patient code, by means of the combination of the patient code with the unique identification code.

3. The method according to claim 1, in which said unique identification code is placed on the corresponding container in a machine readable format.

4. The method according to claim 3, in which the combination of the patient code with the unique identification code is generated by the sequential reading by an automatic reading instrument of the patient code and the unique identification code, or vice versa.

5. The method according to claim 1, in which said patient code is placed on a medium in a machine-readable formal.

6. The method according to claim 1, in which said patient code and said unique identification code are reproduced as bar codes and are optically read to produce said combination.

7. The method according to claim 1, in which said patient code is generated by a central computer of said data processing system; the combination of the patient code with the unique identification code is carried out by means of a unit of said data processing system other than said central computer; and the result of the analysis, associated with the patient code, is sent to said central computer.

8. The method according to claim 1, in which said patient code is generated by a central computer of said data processing system; the combination of the patient code with the unique identification code is carried out by means of a unit of said data processing system other than said central computer, and the result of the analysis, associated with the unique identification code of the container, is sent to said central computer, the central computer being programmed to associate with the result of the analysis the data relating to the patient to whom said result relates.

9. The method according to claim 1, further comprising;
connecting a means to each container for determining an expiry date of the respective container.

10. A data processing system for data management in an analytical laboratory, the system comprising, in combination,
a central electronic computer, for acquiring the data on patients on whose biological specimens the analyses are to be carried out, and for generating a patient code for each patient acquired;
means for acquiring a unique identification code associated with each container of a plurality of containers for laboratory analysis of biological specimens;
a marking with said unique identification code, said marking being applied to said container during production or packaging of the container;
means for combining each of said acquired unique identification codes with a corresponding patient code to form combined database on said unique identification code and said patient code;
at least one analyzer with means for reading the unique identification codes associated with the containers which are placed in said at least one analyzer, said analyzer carrying out at least one analysis on a biological specimen contained in the containers placed in said at least one analyzer and supplying to said electronic computer the result of the analyses carried out, combined with data capable of associating said result with the patient to whom the biological specimen belongs based on said combined data.

11. The system according to claim 10, comprising means for receiving from said at least one analyzer the result of said at least one analysis combined with the unique identification code of the container in which the analyzed biological specimen is placed; said means being programmed to associate said result with the patient code relating to the unique identification code combined with the result of the analysis, to send the result of the analysis combined with the patient code to said central electronic computer.

12. The system according to claim 10, in which the result of the analysis, combined with the unique identification code of the corresponding container, is sent to said central computer, the central computer being programmed to associate, by means of the combination of the patient code with the unique identification code, each unique identification code—and consequently the result of the analysis—with the patient code of the patient whose biological specimen is contained in the container identified by said unique identification code.

13. The system according to claim 10, further comprising:
means connected with each container for determining an expiry date of the respective container.

14. An analytical laboratory data management method comprising the steps of:
generating unique identification codes;
providing a plurality of containers for the laboratory analysis of biological specimens;
associating each of said containers with one of said unique identification codes and applying a marking including said unique identification code to the associated container during production or packaging of the container at a first location;
generating patient codes with a host computer or providing as input into the host computer the generated patient codes;
associating each patient code with an individual patient to be subjected to analysis;
providing, at a second location, a biological specimen from the individual patient with the associated patient code in the container with said marking including said unique identification code;
providing correlation data, based on a combination of said patient code and the marked said unique identification code of the corresponding container for which the biological specimen has been or will be provided, by reading or receiving said patient code and reading the marked said unique identification code of the corresponding container having the biological specimen, said correlation data being provided to a device separate from said host computer,
providing an analyzer for analysis of the biological specimen;
carrying out at least one analysis on the container, with the unique identification code having the biological specimen, using the analyzer to provide results of the analysis associated with the unique identification code;
associating the results of the analysis with the patient code at the device separate from the host computer based on the correlation data; and
sending the results of the analysis and associated patient code to the host computer.

15. The method according to claim 14, further comprising: connecting a means to each container for determining an expiry date of the respective container.

16. An analytical laboratory data management method comprising the steps of:
generating unique identification codes;
providing a plurality of containers for the laboratory analysis of biological specimens;
associating each of said containers with one of said unique identification codes and applying a marking including said unique identification code, to the associated container during production or packaging of the container at a first location;

generating patient codes with a host computer or providing as input into the host computer the generated patient codes;

associating each patient code with an individual patient to be subjected to analysis;

providing, at a second location, a biological specimen from the individual patient with the associated patient code in the container with said marking including said unique identification code;

providing correlation data based on a combination of said patient code and the marked said unique identification code of the corresponding container for which the biological specimen has been or will be provided, by reading or receiving said patient code and reading the marked said unique identification code of the corresponding container having the biological specimen;

providing an analyzer for analysis of the biological specimen;

carrying out at least one analysis on the container, with the unique identification code having the biological specimen, using the analyzer to provide results of the analysis associated with the unique identification code;

sending the results of the analysis associated with the unique identification code to the host computer; and associating the results of the analysis with the patient code at the host computer based on the correlation data.

17. The method according to claim 16, further comprising:

connecting a means to each container for determining an expiry date of the respective container.

18. A set of containers for laboratory analysis of biological specimens, each container of the set comprising:

a container body;

a marking or label connected to said container body and having or embodying a machine-readable identification code that is unique to said container body relative to other identification codes of the set of containers, said marking or label with said machine-readable identification code being associated with said container body and applied to said container body during production or packaging of said container body; and means connected with said container body during production or packaging of said container body for determining an expiry date.

19. The container according to claim 18, wherein said identification code is a bar code.

* * * * *